US00PP30308P2

(12) United States Plant Patent
Griffith et al.

(10) Patent No.: US PP30,308 P2
(45) Date of Patent: Mar. 26, 2019

(54) ***HYDRANGEA MACROPHYLLA* PLANT NAMED 'GRIFFHY-01'**

(50) Latin Name: *Hydrangea macrophylla*
Varietal Denomination: GRIFFHY-01

(71) Applicant: Griffith Propagation Nurseries Inc., Watkinsville, GA (US)

(72) Inventors: Mark Griffith, Watkinsville, GA (US); Rhonda Helvick, Watkinsville, GA (US); Ben Sanders, Watkinsville, GA (US)

(73) Assignee: Griffith Propagation Nurseries Inc., Watkinsville, GA (US)

( * ) Notice: Subject to any disclaimer, the term of this patent is extended or adjusted under 35 U.S.C. 154(b) by 0 days.

(21) Appl. No.: 15/932,397

(22) Filed: Feb. 23, 2018

(51) Int. Cl.
*A01H 5/02* (2018.01)

(52) U.S. Cl.
USPC ..... Plt./250

(58) Field of Classification Search
USPC ..... Plt./226, 250
See application file for complete search history.

*Primary Examiner* — Susan McCormick Ewoldt
*Assistant Examiner* — Karen M Redden
(74) *Attorney, Agent, or Firm* — Leydig, Voit & Mayer, Ltd.

(57) ABSTRACT

A new and distinct cultivar of *Hydrangea macrophylla* plant named 'GRIFFHY-01', characterized by its bright yellow foliage color, remontant (reblooming) trait, flowering on old wood and new growth of the season, pink mophead inflorescence in non-aluminium based media and blue inflorescence in aluminum based media, and compact, rounded to spreading growth habit.

4 Drawing Sheets

Genus and species of plant claimed: *Hydrangea macrophylla.*

Variety denomination: 'GRIFFHY-01'.

BACKGROUND OF THE INVENTION

The present invention relates to a new and distinct cultivar of *Hydrangea macrophylla*, a member of the Hydrangeaceae family, hereinafter referred to by its cultivar name 'GRIFFHY-01'. This cultivar is grown primarily as an ornamental for landscape use and for use as a potted plant. The cultivar originated from a naturally occurring, non-induced branch mutation of *Hydrangea macrophylla* 'Penny Mac' (not patented) in 2015, in Watkinsville, Ga. and was selected and continually evaluated for foliage color, growth habit, and floral characteristics.

'GRIFFHY-01' has been asexually reproduced by softwood cuttings since 2015 in Watkinsville, Ga. The characteristics of the cultivar have been stable and reproduced true to type in successive vegetative generations.

SUMMARY OF THE INVENTION

'GRIFFHY-01' has not been observed under all possible environmental conditions. The phenotype may vary somewhat with changes in light, temperature, soil and rainfall without, however, any variance in genotype.

The following traits have been observed and represent the characteristics of the new cultivar. In combination, these characteristics distinguish 'GRIFFHY-01' from all other varieties in commerce known to the inventor. 1) Bright yellow foliage. 2) Remontant (reblooming) trait, flowering on old wood and new growth of the season. 3) Pink mophead inflorescence in non-aluminum based media and blue inflorescence in aluminum based media. 4) Compact, rounded to spreading growth habit. 5) Increased mildew resistance as compared to some cultivars.

'GRIFFHY01' is distinguished from its parent plant *Hydrangea macrophylla* 'Penny Mac' (not patented) by its foliage color. 'GRIFFHY-01' has bright yellow foliage, whereas 'Penny Mac' has green foliage.

'GRIFFHY-01' can be compared to the cultivar 'Lemon Daddy' (U.S. Plant Pat. No. 17,660) but differs in the following characteristics. 'GRIFFHY-01' reblooms throughout the growing season on old and new wood, whereas 'Lemon Daddy' does not flower on new growth. 'GRIFFHY-01' holds its golden-yellow color throughout the growing season; whereas the foliage on 'Lemon Daddy' tends to turn green with heat as the season progresses. 'Lemon Daddy' has thick textured leaves, whereas 'GRIFFHY-01' has thinnish foliage.

'GRIFFHY-01' can be compared to the cultivar *Hydrangea macrophylla* 'Yellowleaf' (U.S. Plant Pat. No. 12,701), but differs in the following characteristics. 'Yellowleaf' has thick golden-yellow foliage, is very frost sensitive, and has no rebloom, whereas 'GRIFFHY-01' has bright yellow foliage, has normal tolerance to frost, and has rebloom on new wood.

BRIEF DESCRIPTION OF THE DRAWINGS

The accompanying illustrations show characteristics of the new cultivar in photographs as true to color as is reasonably possible to make in illustrations of this nature. Colors in the photographs may differ slightly from the color values cited in the detailed botanical description which accurately describe the colors of the new *Hydrangea.*

DETAILED DESCRIPTION

Figure 1:
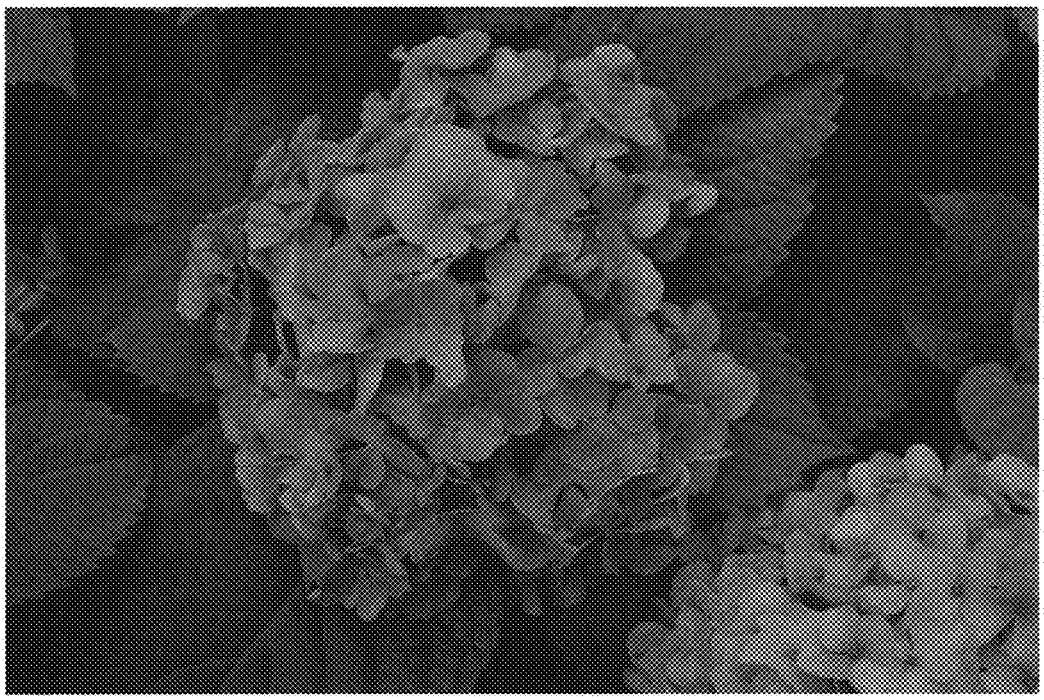
FIG. 1 shows a two-year-old 'GRIFFHY-01' plant grown with aluminum.
Figure 2:
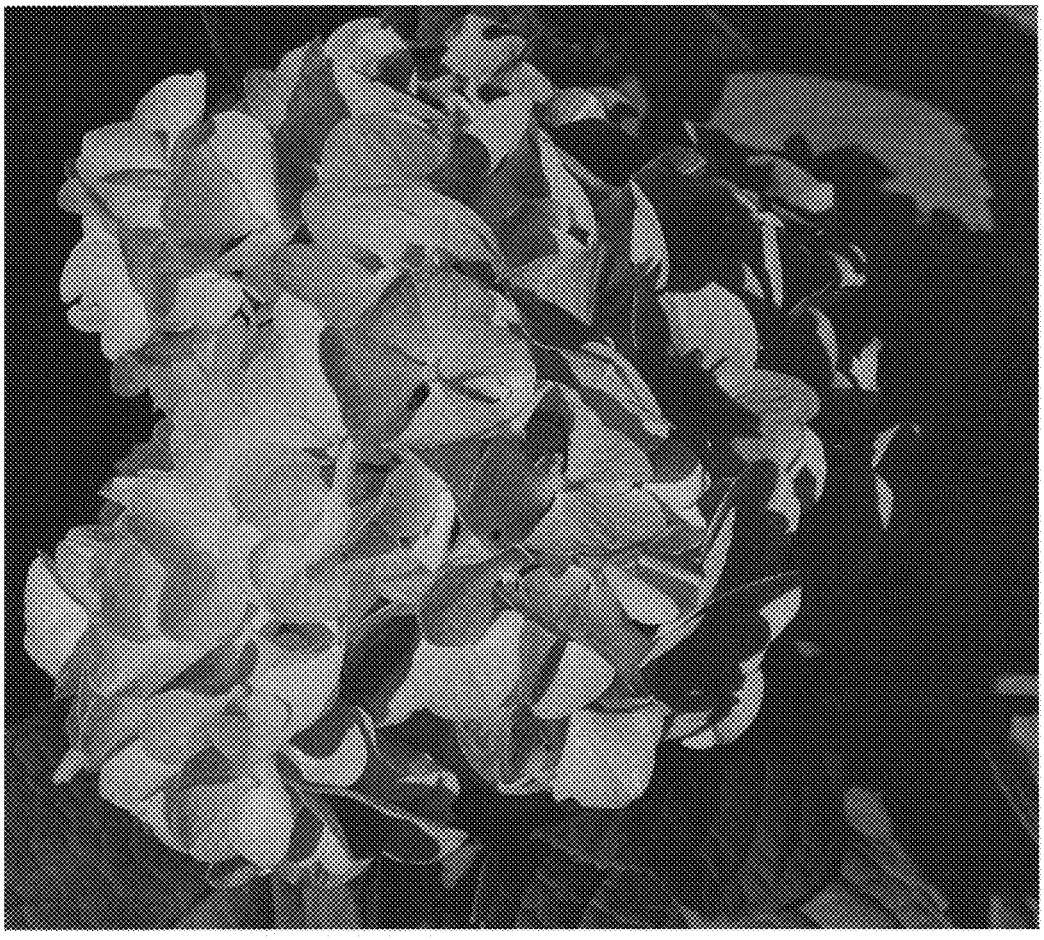
FIG. 2 shows a two-year-old 'GRIFFHY-01' plant grown in absence of aluminum.
Figure 3:
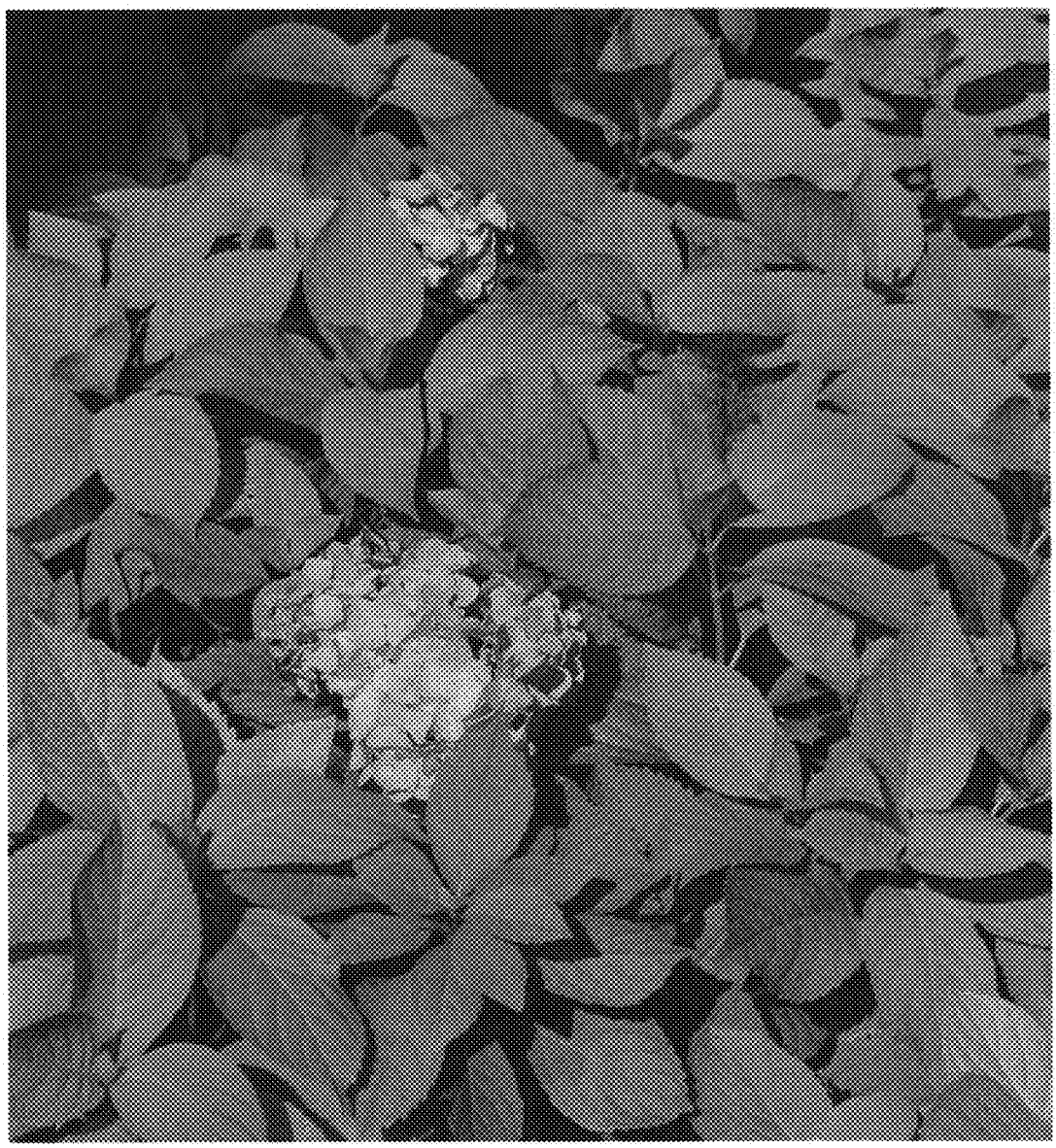
FIG. 3 shows a two-year-old 'GRIFFHY-01' foliage in the summer.
Figure 4:
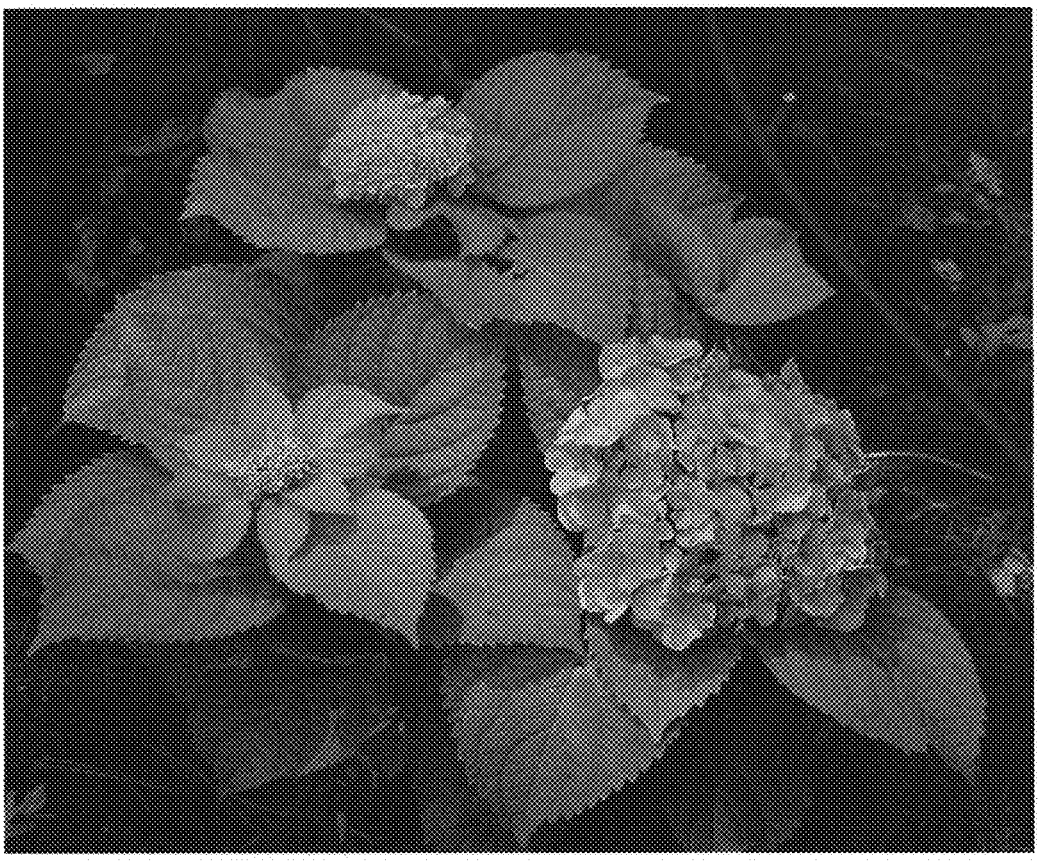
FIG. 4 show a mature two-year-old 'GRIFFHY-01' grown in a 3 gal container.

In the following description, color references are made to The Royal Horticultural Society Colour Chart, 2015 Edition, except where general terms of ordinary dictionary significance are used. Plants used for the description were grown in 11.4 L containers under 50% shade under outdoor conditions in a nursery in Watkinsville, Ga. Plants were about two years old when the description was recorded. Two groups of plants were used for the description to describe the flower colors with and without aluminum. The first group was grown in a medium consisting of composted pine bark, with no aluminum present and a pH of 5.4. The second group was grown in a medium consisting of composted pine bark that was amended with 63 grams of aluminum sulphate and a pH of 5.3. Aluminum only affects flower color. Therefore, colors with and without aluminum are only specified for floral parts.

Botanical classification: 'GRIFFHY-01' is a cultivar of *Hydrangea macrophylla.*

*Parentage.*—The current variety is a progeny from a naturally occurring, non-induced branch mutation of *Hydrangea macrophylla* 'Penny Mac' (not patented).

*Propagation.*—Vegetatively by stem cuttings. Time to initiate roots in the summer about 14 days at 32° C. Time to produce a young rooted plant, summer about 3 months at 32° C. Time to produce a finished crop in a 11.4 L container potted with a 0.041 L liner pot about 9 months.

Plant description: The claimed variety is a rounded and spreading deciduous shrub. The original plant, now about 2-years-old in a container, is about 55 cm in height from the soil level to the top of the inflorescences, and about 63 cm in diameter. Freely branching. Pinching enhances branching. There are approximately 4 lateral branches per plant. Quantity of leaves per lateral branch is approximately 14 (7 pairs).

*Stems.*—First year stems have a length of about 24 cm and a diameter of about 4 mm, they are rounded, and smooth in texture. First year stem color is N144D. Second year stems have a length of about 31 cm or longer and a diameter of about 6 mm or more and are N199D in color. Texture of mature stems is woody. Exfoliation begins on second year and older stems, flaky and stringy, the color is 161A. Stem strength: flexible when young, easily broken when mature.

*Root description.*—Numerous, fine, fibrous and well-branched. Color: NN155A.

*Vegetative buds.*—Arrangement: opposite; Shape: ovoid; Size: about 2 mm in length, about 1 mm in width; Color: N144D.

Leaves:

*Size.*—about 17 cm in length and about 14 cm in width. Leaves large and thinnish; simple, opposite and durable.

*Shape.*—Ovate, with acuminate apex, cuneate base and serrate margin.

*Texture.*—Upper surface glabrous; lower surface glaucescent. No pubescence.

*Color.*—Emerging leaves are N144B on the upper surface and 151A on the lower surface; mature leaves on the upper surface are 151A mixed with some N144A, and 144C on the lower surface. Winter Leaf Color: insignificant.

*Venation.*—Pinnate, veins. Veins on emerging foliage and fully expanded foliage upper surface: 144A and lower surface: 147D.

*Petiole.*—About 1.3 cm in length and about 2.5 mm in diameter, upper and lower surface smooth and glabrous, and 149C in color. Petiole is grooved on upper side and crescent-shaped in cross section.

Flowers:

*Inflorescence bloom period.*—Early summer to first frost in fall. An inflorescence contains about 68 individual fertile flowers. An inflorescence contains about 350 individual sterile florets.

*Inflorescence shape and size.*—Mophead, about 10 cm in height and about 21 cm in diameter. The inflorescence is effective for about 8 weeks, and no fragrance is detected. The peduncle is angled upright and is moderately strong and flexible, about 5.5 cm in length and 4 mm in diameter, and is N144D in color with and without aluminum. The pedicels angle about 45° from vertical, with a length about 1.2 cm and diameter of about 1 mm are moderately strong and flexible, 98D in color with aluminum and 62C in color without aluminum.

*Flower bud size.*—About 6 mm in length, about 4 mm in width prior to opening.

*Flower bud shape.*—Round; Color 145B to 145C prior to opening. Once it begins to open color: 100A when grown with aluminum, and 62B when grown without aluminum. Sterile florets are about 3 cm in diameter. Each floret contains 4 sepals about 2 cm in length and about 1.5 cm in width.

*Sterile floret shape.*—Ovoid with obtuse apex, acute base, and entire margin.

*Texture.*—Smooth with no pubescence.

*Color at maturity.*—With aluminum, the upper surface is 101C and the lower surface is 97B. Without aluminum, the upper surface is 73C and lower surface is N73D.

*Color of aged sepals.*—With aluminum, the upper surface 85C and lower surface 85D. Without aluminum, the upper surface 155B with a hint of 62D and the lower surface 155C with a hint of 62D.

*Petals (fertile flowers).*—

*Size.*—5 petals per flower, about 3 mm in length and about 1.5 mm in width.

*Shape.*—Ovate, with acuminate apex, truncate base, and entire margin.

*Texture.*—Smooth with no pubescence.

*Color.*—At peak of bloom the upper surface of the petals is 100B and the lower surface is 100C with aluminum. When grown without aluminum the upper surface of the petals is 63C and the lower surface is 63D.

*Sepals.*—5 per flower, 1.5 mm in length and 0.75 mm in width.

*Color of sepal.*—On upper and lower surface with aluminum 100C.

*Color of sepal*.—On upper and lower surface 63C without aluminum.

*Number of stamens*.—4 to 5 per flower.

*Anthers*.—About 1 mm in length and about 0.5 mm in width, 100B in color with aluminum and 62D in color without aluminum.

*Filaments*.—About 3 mm in length and 100B in color with aluminum and 62C in color without aluminum.

*Pollen*.—155D in color, produced in moderate quantities.

*Pistil*.—Superior, about 3 mm in length and about 1.5 mm in width, 100B in color with aluminum and 63B in color without aluminum.

*Stigma*.—Usually 2 but sometimes 3 per pistil, round in shape and 100B in color with aluminum and 62B in color without aluminum.

*Style*.—About 2 mm in length and tubular in shape, 100A in color with aluminum and 85D in color without aluminum.

Fruit: The capsule fruit is ovoid, about 3 mm in length and about 2 mm in width. The color during early ripening is close to 54B and at maturity is close to 200C. The number of fruit per infructescence varies widely. Seed: The seeds are round, about 0.5 mm in length and about 0.5 mm in width, close to 199B, and each capsule contains about 50 seeds.

Plant hardiness:

*Plant hardiness*.—USDA Hardiness Zone Map (2012): Zones 5-9.

Disease/pest resistance: Resistant to powdery mildew. No other pest or disease resistance/susceptibility has been observed.

We claim:

1. A new and distinct *Hydrangea macrophylla* plant named 'GRIFFHY01', substantially as illustrated and described herein.

* * * * *